(12) United States Patent
Bauman et al.

(10) Patent No.: US 8,641,761 B2
(45) Date of Patent: Feb. 4, 2014

(54) CREATION AND IMPLANTATION OF AN ARTIFICIAL NAIL FOR THE TREATMENT OF DEFORMED OR MISSING NAILS

(75) Inventors: Mark Bauman, Marlton, NJ (US);
James Nolan, Branford, CT (US)

(73) Assignee: Mark Bauman, Marlton, NJ (US)

( * ) Notice: Subject to any disclaimer, the term of this patent is extended or adjusted under 35 U.S.C. 154(b) by 187 days.

(21) Appl. No.: 13/187,810

(22) Filed: Jul. 21, 2011

(65) Prior Publication Data

US 2011/0276065 A1 Nov. 10, 2011

Related U.S. Application Data

(63) Continuation-in-part of application No. 13/049,961, filed on Mar. 17, 2011, now abandoned.

(60) Provisional application No. 61/315,182, filed on Mar. 18, 2010.

(51) Int. Cl.
*A61B 17/08* (2006.01)
*A61F 2/10* (2006.01)
*A61B 19/00* (2006.01)

(52) U.S. Cl.
USPC .................. 623/15.11; 606/151; 128/898

(58) Field of Classification Search
USPC ......... 623/11.11, 15.11–15.12; 606/151–152; 128/898
See application file for complete search history.

(56) References Cited

U.S. PATENT DOCUMENTS

| | | | | |
|---|---|---|---|---|
| 4,847,962 | A | * | 7/1989 | Puetz .................. 29/898.02 |
| 5,060,678 | A | * | 10/1991 | Bauman et al. ............ 132/73 |
| 2005/0263388 | A1 | * | 12/2005 | Lee et al. .............. 204/192.1 |
| 2006/0147492 | A1 | * | 7/2006 | Hunter et al. ............ 424/426 |

* cited by examiner

*Primary Examiner* — David Isabella
*Assistant Examiner* — Yashita Sharma
(74) *Attorney, Agent, or Firm* — Novak Druce Connolly Bove + Quigg LLP

(57) ABSTRACT

The creation and implantation of an artificial nail in the treatment of deformed or missing nails includes preparing the nail bed. A polypropylene mesh is applied and anchored to the nail bed. Nail restoration material is applied to the polypropylene mesh. The nail restoration material is secured by regenerated nail tissue growing through the openings of the mesh whereby the mesh acts as an interface for the nail bed and the nail restoration material.

9 Claims, 5 Drawing Sheets

CREATION AND IMPLANTATION OF AN ARTIFICIAL NAIL FOR THE TREATMENT OF DEFORMED OR MISSING NAILS

CROSS-REFERENCE TO RELATED APPLICATION

This application is a continuation in part of application Ser. No. 13/049,961, filed Mar. 17, 2011 now abandoned, which is based upon provisional application Ser. No. 61/315,182 filed Mar. 18, 2010, all of the details of these applications are incorporated herein by reference thereto.

BACKGROUND OF INVENTION

The present invention relates to the creation of artificial nails. Various techniques have been used in the past to create artificial nails. These techniques have had differing degrees of effectiveness. U.S. Pat. No. 5,060,678 discloses artificial nail and implantation techniques.

SUMMARY OF THE INVENTION

An object of this invention is to provide techniques for the creation and implantation of an artificial nail for the treatment of deformed or missing nails.

In accordance with this invention a mesh is anchored to a raw nail bed. Nail restoration material is applied to the mesh. The nail restoration material is secured to regenerated nail tissue which grows through the openings of the mesh so that the mesh functions as an interface.

THE DRAWINGS

FIGS. 1-11 illustrate the steps involved in the creation and implantation of an artificial nail in accordance with this invention.

DETAILED DESCRIPTION

The present invention is directed to the creation of artificial nails. It is to be understood that the practice of this invention may be accomplished for either toenails or fingernails.

In general, the invention may be practiced by utilizing an established technique nail matricectomy which is performed by a chosen method on the patient's toe or finger while an appropriate tourniquet has already been placed around the digit, and the digit has been anesthetized.

Figure 1:
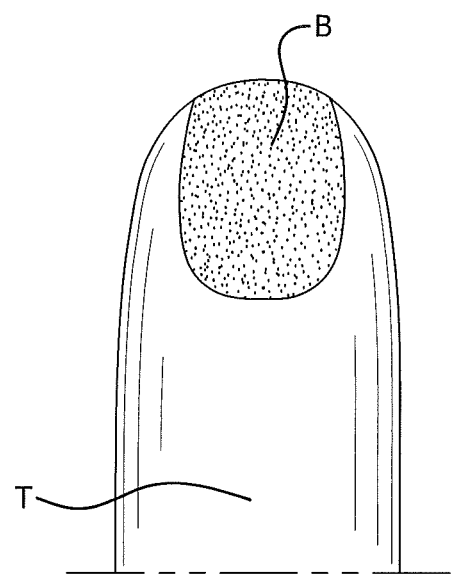
Figure 2:
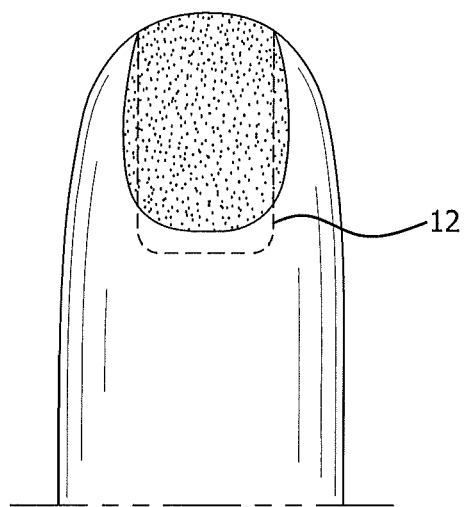
Figure 3:
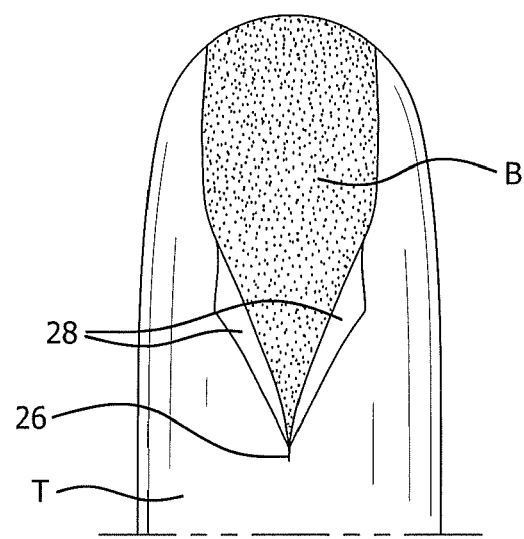

FIGS. 1-6 show the various steps in preparing the digit which as illustrated is a toe T. In general, as later described, a raw nail bed B is created as shown in FIG. 1. While the nail bed and matrix are excised sharply, leaving the most distal aspect of nail bed intact, the medial and lateral nail folds 28,28 and eponychium are also incised sharply to create a U-shaped channel 12, with the open end of the "U" facing distally. See FIGS. 2-3.

Figure 4:
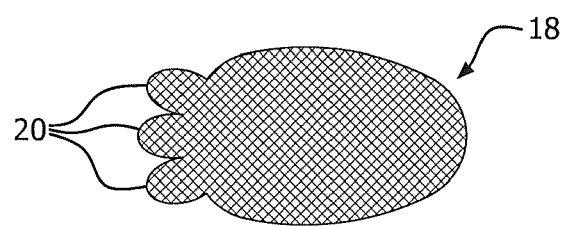

An appropriate-sized sterilized mesh 18 preferably made of polypropylene, is selected, such as shown in FIG. 4. The mesh 18 is carefully placed onto the digit T and the medial and lateral wings of the mesh 18 are carefully placed under the medial and lateral nail folds 28,28, while the three proximal anchor points 20 are carefully placed under the exposed eponychium. See FIG. 5.

The eponychial area may be sutured at the discretion of the surgeon. At the level of the hyponychium, a continuous suture 14 of a small gauge is placed between the mesh and most distal nail bed to create a distal anchorage of the mesh 18.

Figure 6:
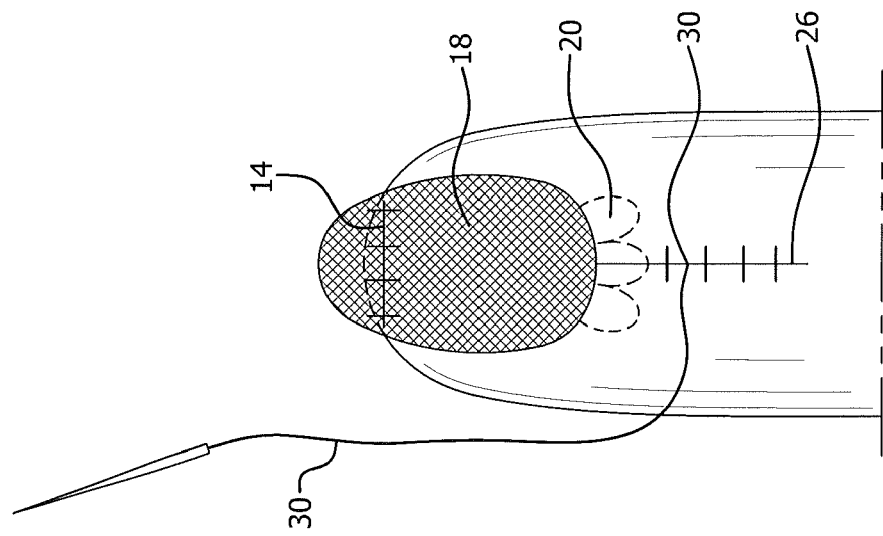
Figure 5:
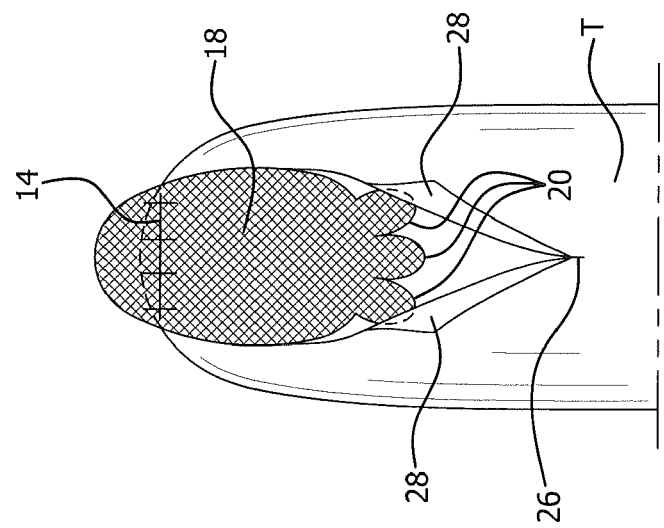
Figure 7:
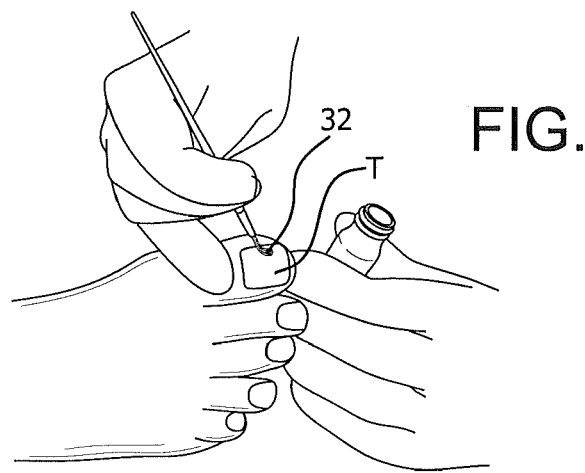
Figure 8:
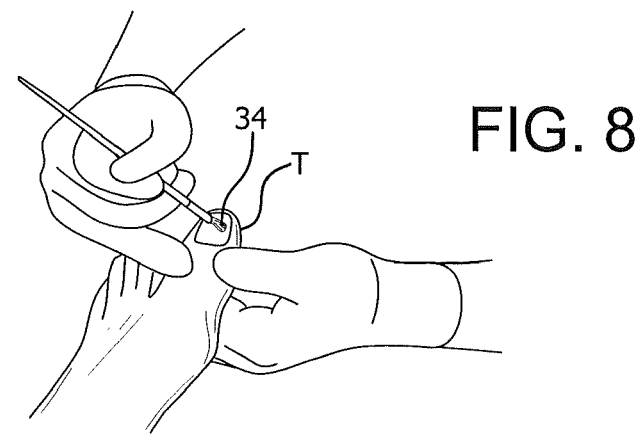
Figure 9:
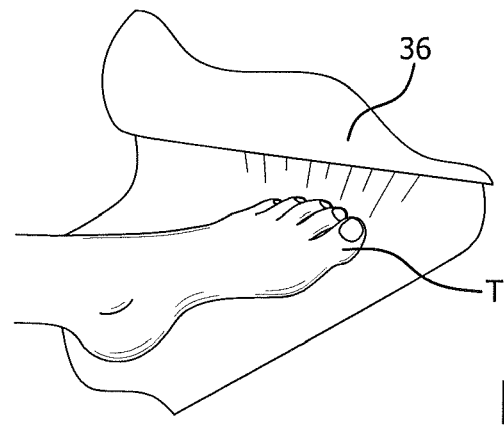

As shown in FIG. 6 the folds or flaps 28,28 are sutured by suture 30 beginning at the proximal incision 26 so that the anchor points 20 of mesh 18 are covered. Mesh 18 is thus firmly anchored in place by the suturing 30 and suturing 14 as well as its positioning in channel 12. FIG. 6 shows the thread-like suture 30 being applied by a suitable needle.

A non-adherent bandage is placed over the wound, and a compression bandage is placed over this bandage, while the tourniquet is released. The post-operative course is examined by the surgeon during the subsequent two weeks.

The artificial nail 18 works by allowing tissue ingrowth to occur. When the individual's digital nail is removed, collagen bonds are broken, causing bleeding and a wound. The healing mechanism for all wounds causes various chemicals to be released in an attempt to heal the wound. Ultimately a scab is formed. By placing the polypropylene mesh 18 about the nail folds and eponychium, as well as at the hyponychium, a scaffolding mechanism will take place within the healing wound, "locking" the mesh to the surrounding tissues.

To create a raw or exposed nail bed B, in instances where there is no existing nail, the cornified nail bed is removed (again leaving the most distal nail bed intact), causing the same type of wound and healing mechanism to occur.

The mesh 18 is of optimal pore size to allow for ingrowth. Polypropylene is a preferred mesh material because it also has strong tear resistance, as well as being minimally reactive, so that little to no foreign body reaction should take place, eliminating the likelihood of rejection of the mesh.

When the matrix (i.e. the center growth or tissue of the nail) is either destroyed (via chemical, laser, etc.) or excised (such as in the preparation step of FIG. 1), the ability of the nail to continue to grow or regenerate is severely (if not completely) compromised. Therefore, with perfect matrix removal or destruction, no new nail forms, and the tissue which used to be nail, and which would have regenerated nail tissue, becomes cornified or as thicker skin tissue. This tissue becomes the platform on which nail restoration material can be applied, with the polypropylene mesh 18, with optimal porosity, acting as a perfect interface. As previously described, polypropylene mesh 18 is applied and anchored to the nail bed (by preparing a large channel in the medial and lateral nail folds and eponychium, and in the hyponychium, where it is sutured with simple interrupted sutures).

Any suitable nail restoration nail material may be used. In the preferred practice of this invention the nail restoration material is a system marketed under the name KeryFlex™. KeryFlex™ is a nail restoration system, somewhat similar to a dental bond, whereby a bonding solution is applied (in the practice of this invention) to the mesh 18, then the gel component is applied to the mesh, then the gel is cured via ultraviolet light, then more gel might be applied, then cured, then the sealant is applied, and then cured via ultraviolet light. This cured "nail" may then be gently shaped via emory board or drill. KeryFlex™ is currently used to fill in, in poorly shaped or constituted nails, by first applying the bonding solution to the existing nail, and then following the subsequent steps. KeryFlex™ cannot bond to a non-active or cornified nail bed; therefore, the mesh 18 is implanted to act as a scaffold to allow KeryFlex™ to bond- or actually surround the mesh 18.

The following is a published description of the ingredients for the components of a KeryFlex™ nail restoration system.

| Component | Ingredients |
|---|---|
| Resin | Urethane acrylate oligomer, aliphatic polyesterurethane acrylate, HPMA, polyesterurethane arcrylate, silica, piroctone olamine, BHT, p-hydroxyanisole, hydroquinone Clear: Methylbenzoylformiate Opaque: Titanium dioxide, Methylbenzoylformiate Pastel: Titanium dioxide, C1 45410:2, C1 15850, methylbenzoylformiate |
| Bond | Alcohol, HEMA, aqua (Water), acylphosphine, pentaerythrityl tetra-di-t-butyl hydroxyhydrocinnamate, piroctone olamine, BHT, p-hydroxyanisole |
| Sealant | DI-HEMA Trimethylhexyl dicarbamate, polyethepolyol tetraacrylate, polyesterurethane acrylate, silica, acylphosphine, benzoyl isopropanol, BHT, p-hydroxyanisole |

As indicated above the KeryFlex™ is a nail restoration system that uses polymer resins and activators to create a durable, yet flexible artificial nail when exposed to a certain frequency of ultraviolet light. In practice KeryFlex™ is a nail restoration system designed to create a cosmetically pleasing appearance of the nail. The system creates an artificial, but natural appearing nail by utilizing synthetic resins that are cured by an ultraviolet light. The resin gel is presently available in three colors: pastel, clear and natural. The system works by creating a flexible, nonporous artificial nail which looks and feels completely natural and is unaffected by acetone, nail polish and detergents. Because it is a flexible polymer, not a ridge acrylic, it adheres better and will not pop off.

Although any suitable nail restoration material may be used in the broad practice of this invention, a KeryFlex™ nail restoration system is preferred.

As previously discussed and illustrated in the drawings, the procedure of this invention involves removal or destruction of the nail and nail matrix to create a raw nail bed B; when that is accomplished, the polypropylene mesh 18 is implanted; when wound is stable (no drainage), nail restoration material is applied to the mesh that has been implanted to the digit T.

At approximately two weeks, by which time the wound should have fully healed, the nail restoration material treatment should be ready for implementation.
The nail bed of digit T will be prepared with an application of the bonding agent 32, such as by brush application, and allowed to dry for two minutes. See FIG. 7.

When the surface is dry, the chosen shade (clear, natural, or opaque) of resin material 34 is carefully applied (such as by brushing) to the meshwork on the nail bed. This is gently sculpted to create a layer of "nail". Care is taken to not allow the resin to fall onto tissue where there is no mesh. See FIG. 8.

When the mesh is covered with resin to a reasonable depth and breadth, the resin is exposed to light from ultraviolet lamp 36 for two minutes, causing the resin to polymerize and harden. See FIG. 9.

The practitioner determines if a second layer of resin is needed to create a thicker or fuller nail. If so, the same protocol is utilized as was done in the previous step, again taking care to not allow the resin to fall onto non-mesh tissue, and utilizing the ultraviolet lamp. The nail can then be "formed", as necessary, using either a soft file or drill bur.

Figure 10:
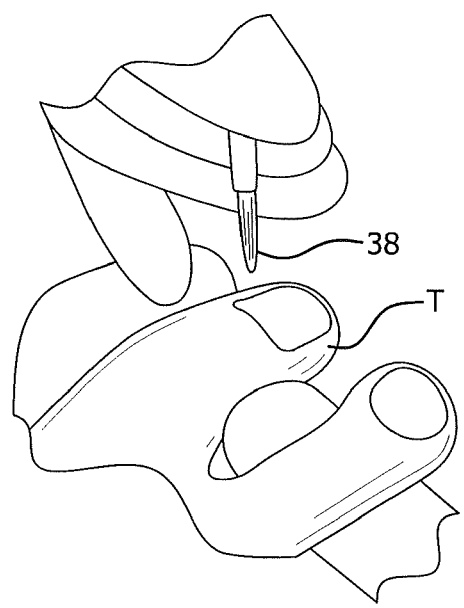
Figure 11:
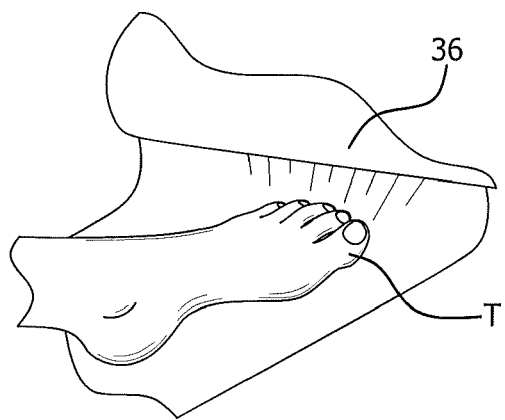

If the surgeon judges the new nail to be sufficient, corresponding to an acceptable level relative to the end of the toe, the sealing agent 38 is then applied (as by, brushing) as shown in FIG. 10. The sealing agent is cured for two minutes with ultraviolet lamp 36. See FIG. 11.

Upon completion of this step, additional fine remodeling can be performed. Nail polish, at the discretion of the patient, can be applied almost immediately.

The materials of which the artificial nail is comprised have been used in the United States and other countries for some time. Medical grade polypropylene is used in, among other areas, hernia repair, vascular surgery, etc. While polypropylene is the preferred material for the mesh 18, the invention may be broadly practiced with any other suitable mesh material.

Only a known allergy to polypropylene, the chemicals which comprise KeryFlex, an open digital growth center, or any condition which would contraindicate the permanent removal of a digital nail and/or matrix would otherwise disqualify one's ability to undergo this procedure and treatment.

The invention may be practiced by having the appropriate components available in a kit. Such a kit would include the mesh 18 and the components of the nail restoration system, namely, the bonding agent, the resin or gel and the sealing agent. The mesh would be of a size and shape corresponding to the nail bed or the digit on which it is intended to be used. If desired the mesh may be initially oversized and then trimmed to the proper size and shape.

A significant feature of this invention is the utilization of the mesh 18 to act as an interface for the nail restoration material and the tissue regeneration. As the artificial nail is attached to the nail bed B by cohesion, the bond is permanent and thus is stronger and more mechanically sound than simple adhesion. The three anchor points 20 on the proximal edge of mesh 18 take up most of the mechanical stress which mimics a natural nail. The bonding which occurs peripherally is similar to what is found naturally that being the microadhesions which secure the nail plate to the underlying nail bed. Fibroblasts are generated from the created wound and should migrate along the collagen fibers which are adhered to the roughened, mesh-configured surface porous implant. Resin is chosen as the artificial nail material due to its inherent strength, history of biocompatibility, its ability to withstand erosion and abrasion, and its ability to be colored either industrially (to create the original color) or by items such as nail polish.

The procedure itself has no untoward effects, save the possible sensitivity one may have to the material (but the lack of a nail often creates a greater sensitivity which is quite evident post-operatively with patients who learn to accept it). If the nail produced by the practice of this invention would need to be removed, an additional surgical intervention would be required. In the case of injury to the digit where the nail implant was partially destroyed or damaged, a replacement nail could be reapplied in the same fashion as the original implant surgery. The procedure affords the patient cosmetic relief for a perceived unsightly condition and enhances both beauty and self-assuredness and a general feeling of comfort in society. The invention provides a more permanent and acceptable alternative to the current status quo; it also increases by its very design and application, a higher level of acceptance on the part of the general population and affords a cosmetic as well as functional (as relates to sensation) correction of those who desire.

What is claimed is:

1. A method of creating and implanting an artificial nail in the treatment of deformed or missing nails from a digit comprising creating a raw nail bed on the digit, applying a mesh to the raw nail bed, anchoring the mesh to the nail bed, applying nail restoration material to the mesh, securing the nail restoration material to regenerated nail tissue with the mesh being an interface, and the mesh and nail restoration material comprising the artificial nail which remains secured to the digit, and wherein the nail restoration material comprises a bonding solution and a gel component and a sealing agent, including the steps of applying the bonding solution to the mesh, then applying the gel component to the mesh, curing the gel component to polymerize and harden the gel component, and then applying the sealing agent.

2. The method of claim 1 wherein the gel is cured by ultraviolet light, and curing the sealing agent by ultraviolet light.

3. The method of claim 1 wherein the mesh is a polypropylene mesh.

4. The method of claim 1 wherein the nail bed is incised to form medial and lateral nail folds and eponychium to create a U-shaped channel with the open end of the U facing distally, placing the mesh on the nail bed, and placing the medial and lateral wings of the mesh under the medial and lateral nail folds.

5. The method of claim 4 including placing anchor points of the mesh under the exposed eponychium.

6. The method of claim 4 including suturing the mesh to the most distal nail bed to create anchorage.

7. The method of claim 6 including suturing the medial and lateral folds of the nail to the bed.

8. The method of claim 7 including locking the mesh to the bed by regenerated nail tissue growing into the mesh openings.

9. The method of claim 8 including forming the raw nail bed by removal or destruction of any nail or nail matrix on the bed and leaving the most distal aspect of the nail intact.

* * * * *